(12) United States Patent  
Graef et al.

(10) Patent No.: US 7,485,706 B2  
(45) Date of Patent: Feb. 3, 2009

(54) NEURODEGENERATIVE PROTEIN AGGREGATION INHIBITION METHODS AND COMPOUNDS

(75) Inventors: Isabella A. Graef, Woodside, CA (US); Gerald R. Crabtree, Woodside, CA (US); Jason E. Gestwicki, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 418 days.

(21) Appl. No.: 10/901,848

(22) Filed: Jul. 28, 2004

(65) Prior Publication Data

US 2005/0209173 A1   Sep. 22, 2005

Related U.S. Application Data

(60) Provisional application No. 60/491,482, filed on Jul. 30, 2003.

(51) Int. Cl.
| | |
|---|---|
| *C07D 498/18* | (2006.01) |
| *C07D 417/02* | (2006.01) |
| *C07D 211/60* | (2006.01) |
| *C12N 9/00* | (2006.01) |
| *C12Q 1/00* | (2006.01) |
| *A01N 37/18* | (2006.01) |

(52) U.S. Cl. .................. 534/797; 540/456; 546/197
(58) Field of Classification Search .................. 534/797
See application file for complete search history.

(56) References Cited

U.S. PATENT DOCUMENTS

| 5,177,203 | A | * | 1/1993 | Failli et al. ................... 540/456 |
| 5,346,893 | A | * | 9/1994 | Failli et al. ................... 514/183 |
| 5,830,462 | A | | 11/1998 | Crabtree et al. |
| 6,011,018 | A | | 1/2000 | Crabtree et al. |
| 6,150,527 | A | * | 11/2000 | Holt et al. ................... 546/189 |
| 6,316,418 | B1 | | 11/2001 | Crabtree et al. |
| 6,372,712 | B1 | | 4/2002 | Briesewitz et al. |
| 2003/0130484 | A1 | | 7/2003 | Gordon et al. |
| 2007/0054348 | A1* | | 3/2007 | Gestwicki et al. ............. 435/25 |
| 2008/0085238 | A1* | | 4/2008 | Li et al. ...................... 424/1.65 |

FOREIGN PATENT DOCUMENTS

EP   778023   *   6/1997

OTHER PUBLICATIONS

Gestwicki et al., Science, 306(5697), 865-869, Jun. 2004.*
Frid et al., Brain Research Reviews, 53(1), 135-160, Jan. 2007.*
Ishii et al., Neuroscience Letters, 333, 5-8, 2002.*
Lorenzo et al., Proc. Natl. Acad. Sci., 91, 12243-12247, Dec. 1994.*
Gestwicki et al., Bifunctional small molecules as inhibitors of amyloidogenic protein-protein interactions. In: Abstracts of papers, 227th ACS National Meeting, Anaheim CA, Mar. 28-Apr. 1, 2004, MEDI-188, Washington DC: American Chemical Society.

Iida et al. FK506-binding protein-type peptidyl-prolyl cis-trans isomerase from a halophilic archaeum, Halobacterium cutirubrum, Gene. 2000, vol. 256, pp. 319-326.

Briesewitz, et al., "Affinity modulation of small-molecule ligands by borrowing endogenous protein surface", 1999 PNAS USA 96, 1953-8.

Cairo, et al., "Affinity-based inhibition of β-amyloid toxicity", 2002 Biochemistry 41, 8620-9.

Ghanta, et al., "A strategy for Designing Inhibitors of β-amyloid toxicity", 1996 J Biol Chem 271, 29525-28.

Goedert "Alpha-synuclein and Neurodegenerative Diseases", 2001 Nature Reviews/Neuroscience 2, 482-501 (.alpha.-synuclein).

Goedert "Pinning down phosphorylated tau", Nature, 1999, vol. 399, p. 739.

Gordan, D. J. and Meredith, S. C. "Probing the role of backbone hydrogen bonding in β-amyloid fibrils with inhibitor peptides containing ester bonds at alternate positions", (2003) Biochemistry 42:475-485.

Graef, I. A. et al., L-type calcium channel and GRK-3 regulate the activity of NF-Atc4 in hippocampal neuronns, 1999 Nature 401: 1703-1708.

Gordan, D. J. and Meredith, S. C. "Probing the role of backbone hydrogen Bonding in β-amyloid Fibrils with inhibitor peptides containing ester bonds at alternate positions", (2003) Biochemistry 42:475-485.

Hardy and Selkoe "The amyloid hypoythesis of alzheimer's disease: process and problems on the road to therapeutics", 2002 Science 297, 353-6.

Hammarstrom, P. et al., "Prevention of transthyretin amyloid disesae by changing protein misfolding energetics", (2003) Science 299:713-716.

Korth, et al., "Acridine and phenothiazine derivatives as phatmacotherapeutics for prion disease", 2001 PNAS 98, 9836-41.

Kim and Lee, "Fullerence Inhibits β-amyloid peptide aggregation", 2003, Biochem Biophys Res Comm 303, 576-9.

(Continued)

*Primary Examiner*—Fiona T Powers
(74) *Attorney, Agent, or Firm*—Bozicevic, Field & Francis LLP; Bret E. Field

(57) ABSTRACT

Methods and compositions are provided for reducing aggregation of neurodegenerative proteins associated with neurotoxicity or other proteins. The compounds comprise a first domain or targeting element for binding to the target proteins linked to a second domain or recruiting element that binds to an aggregation inhibiting protein, e.g. a prolyl isomerase. By associating the aggregating forming proteins or neuronal cells under conditions where aggregating proteins are produced with the compound and the aggregation inhibiting protein, aggregation is reduced. The subject agents can be used in assays, investigating the etiology of the neuronal diseases and for prophylaxis and therapy.

5 Claims, 10 Drawing Sheets

OTHER PUBLICATIONS

Koo, E. H. et al., "Amyloid diseases: abnormal protein aggregation in neurodegeneration", (1999) Proc. Natl. Acad. Sci. USA 96:9989.

Kayed, R. et al "Common structure of soluble amyloid oligomers implies common mechanism of pathogenesis", (2003) Science 300:486.

Kim, Y-S. et al "Congo red populates partially unfolded states of an amyloidogenic protein to enhance aggregation and amyloid fibril formation", (2003) J. Biol. Chem. 278:10842-10850.

Klettner and Henlegen "FK506 and its analogs- therapeutic potential for neurological disorders", (2003) Curr Drug Target CNS Neurol Disord 2, 152-62-FK506.

Klunk, W. E. et al "Chrysamine-G, a lipophilic analogue of congo red, inhibits Aβ-induced toxicity in PC12 cells", (1998) Life Sciences 63:1807-1814.

Lowe, et al., Structure-function relationships for inhibitors of β-amyloid toxicity containing the recognition sequence KLVFF, 2001 Biochemistry 40, 7882-89.

Lee, 2002 Neurobiology of Aging 23, 1039-42.

Lu, et al., "The prolyl isomerase pin1 restores the function of alzheimer-associated phosphorylated tau protein" 1999 Nature 399, 784-788.

Lee, et al., Neurogenerative Tauopathies 2000 Ann Rev Neurosci 24, 1121-59.

Sacchettini, J. C. and Kelly, J. W. "Therapeutic stategies for human amyloid diseases", (2002) Nature Rev. Drug Discovery 1:267-275.

Spencer, et al., "Controlling signal transduction with synthetic ligards", 1983 Science 262, 1019-24.

Serpell, L. C. "Alzheimer's amyloid fibrils: structure and assembly", (2000) Biochimica et Biophysica Acta 1502:16-30.

Volles, M. J. and Lansbury, P. T. Jr., "Zeroing in on the pathogenic form of α-synuclein and its mechanism of neurotoxicity in parkinson's disease", (2003) Biochemistry 42:7871-7878.

Zoghbi and Orr, "Glutamine repeats and neurodegeneration", 2000 Ann Rev Neurosci 23, 217-47 (glutamine repeats).

* cited by examiner

A

B

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct
<300> PUBLICATION INFORMATION:
<301> AUTHORS: Lowe, T.L., Strzelec, A., Kiessling, L.L., Murphy, R.M.
<302> TITLE: Structure-function relationship for inhibition of
      beta-amyloid toxicity containing the recognition sequence KLVFF
<303> JOURNAL: Biochemistry
<304> VOLUME: 40
<305> ISSUE: 26
<306> PAGES: 7882-9
<307> DATE: 2001-07-03

<400> SEQUENCE: 1

Lys Leu Val Phe Phe
1               5
```

NEURODEGENERATIVE PROTEIN AGGREGATION INHIBITION METHODS AND COMPOUNDS

REFERENCE TO RELATED APPLICATIONS

This application claims priority to provisional application Ser. No. 60/491,482, filed Jul. 30, 2003.

This invention was made in part with government support under Grant No. NS046789 awarded by the National Institutes of Health. The government has certain rights in this invention. This work was also supported by the Howard Hughes Medical Institute.

BACKGROUND OF THE INVENTION

1. Field of the Invention

The invention relates generally to modification of neurodegenerative protein aggregations associated with neuronal disease.

2. Background Information

In an aging population there is an increasing incidence of neurodegenerative diseases. These diseases that waste the mental faculties while still leaving the physical capabilities substantially intact are an emotional drain on those related to the patient and a major financial drain on the patient, patient families and societies. Many of these diseases have certain common features. One of the features is the formation of pathological conformations of proteins that can lead to protofibrils, fibrils and amorphous aggregations resulting in neuronal cell death.

Among the diseases associated with such etiology are Alzheimer's disease, Parkinson's disease, transmissible spongiform encephalopathies, such as Creutzfeld-Jakob disease, polyglutamine diseases, Huntington disease, and Lou Gehrig's disease, as well as other neuropathologies. Efforts to treat these diseases have been substantially unavailing. The efforts have been impeded by the inability to diagnose the diseases at their early stages and recognizing the existence of the disease until the patient becomes symptomatic. Also, there are the problems of the blood brain barrier, the identification of effective drugs and the incidence of side effects of attempted treatments.

Originally, assay methods were developed that relied on cells in culture, which have provided insights into the etiology of these diseases. The effect of various treatments on neuronal mortality has aided in understanding how one may reduce the level of neuronal toxicity of the aggregates. Today, there are mouse models, where the mice have been genetically modified to represent the neuronal pathologies. In this way, experiments can be performed that more readily approximate the human condition.

The Kiessling laboratory, as well as the Lee and Kung laboratories, among others, have done extensive studies on methods of interfering with protein aggregation in amyloid related diseases, e.g. Alzheimer's disease. The Kiessling group has identified an amino acid sequence in A that appears to be a domain involved with aggregation, amino acids 16-20 (KLVFF)(SEQ ID NO:1). Further efforts are needed to provide compounds that can be used in research to elucidate the mechanisms of the neuropathies, the role played by the formation of fibrils and plaques and the effect of interference of such formation. In this way, compounds can be developed that will be used in the treatment of the neuropathies.

Besides the neuropathies associated with aggregation, other diseases may also involve aggregation, where there is an interest in preventing or deterring the aggregation from inducing a diseased state. In addition, there are other situations where the inhibition of aggregate formation, such as in the analysis of naturally occurring mixtures are of interest.

Relevant Literature

Work by the Kiessling group may be found in Ghanta, et al., 1996 J Biol Chem 271, 29525-28; Lowe, et al., 2001 Biochemistry 40, 7882-89 and Cairo, et al., 2002 Biochemistry 41, 8620-9, describing the binding domain of Aβ and assay methodology. Other articles related to Aβ include Korth, et al., 2001 PNAS 98, 9836-41, Hardy and Selkoe 2002 Science 297, 353-6; Lee, 2002 Neurobiology of Aging 23, 1039-42 and Kim and Lee, 2003, Biochem Biophys Res Comm 303, 576-9, where the latter reports that fullerene has an aggregation inhibiting effect on Aβ. Description of the prolyl isomerase Pin 1 and its role with phosphorylated tau is described in Lu, et al., 1999 Nature 399, 739-40; and Lu, et al., 1999 Nature, 399.

Review articles of protein aggregation associated neuropathies include Zoghbi and Orr, 2000 Ann Rev Neurosci 23, 217-47 (glutamine repeats); Lee, et al., 2000 Ann Rev Neurosci 24, 1121-59; Goedert 2001 Nature Reviews/Neuroscience 2, 482-501 (α-synuclein); Sacchettini, J. C. and Kelly, J. W. (2002) Nature Rev. Drug Discovery 1:267-275—a good recent review of inhibitor strategies; Volles, M. J. and Lansbury, P. T. Jr (2003) Biochemistry 42:7871-7878.—discussion of the latest models of Parkinson's pathology; Koo, E. H. et al (1999) Proc. Natl. Acad. Sci. USA 96:9989-9990—one of the most commonly cited reviews on the subject of amyloid diseases; Kayed, R. et al (2003) Science 300:486-489.—suggests that various amyloidogenic peptides display a common mechanism(s) of aggregation; and Serpell, L. C. (2000) Biochimica et Biophysica Acta 1502:16-30—discusses current thinking about the structure of Aβ aggregates.

Other references of interest include references associated with the experimental procedures: Gordon, D. J. and Meredith, S. C. (2003) Biochemistry 42:475-485; and Graef, I. A. et al 1999 Nature 401:1703-1708 and other references associated with inhibitors: Gordon, D. J. and Meredith, S. C. (2003) Biochemistry 42:475-485—inhibitor peptides; Kim, Y-S. et al (2003) J. Biol. Chem. 278:10842-10850—data shows that Congo red binds to unfolded Aβ peptide; Hammarstrom, P. et al (2003) Science 299:713-716.—inhibitors based on kinetics; Klettner and Henlegen (2003) Curr Drug Target CNS Neurol Disord 2, 152-62—FK506 for treatment of neurological disorders; and Klunk, W. E. et al (1998) Life Sciences 63:1807-1814—first chrysamine G paper.

Spencer, et al., 1983 Science 262, 1019-24 describes the construction of small molecules that are dimeric and bind two different proteins created by DNA recombination. See also, U.S. Pat. Nos. 5,830,462; 6,011,018 and 6,316,418. Briesewitz, et al., 1999 PNAS USA 96, 1953-8 and U.S. Pat. No. 6,372,712 describe the use of an endogenous protein to modulate the affinity of a small molecule.

SUMMARY OF THE INVENTION

The presence of protein aggregations, particularly as associated with neuropathies or other environments in which aggregation is detrimental, are diminished by adding to an environment in which such protein aggregations occurs a compound having two domains, one that targets aggregations and a second that recruits proteins to the site of aggregation, particularly prolyl isomerases or other applicable proteins, by binding to the aggregate forming protein. The compounds are characterized by having a domain that preferentially binds to aggregations comprising at least two monomeric proteins linked to a second domain that recruits the aggregation modifying protein(s). In the case of neuropathies, the presence of prolyl isomerases intra- and extracellular ensure the availability of the aggregation modifying protein, as well as the opportunity to modify the aggregate monomer by isomerizing proline to reduce the propensity to form aggregates as well as sterically hinder aggregate formation. Of particular interest are domains of compounds that when combined are able to cross the blood brain barrier.

DETAILED DESCRIPTION OF THE INVENTION

Figure 1:
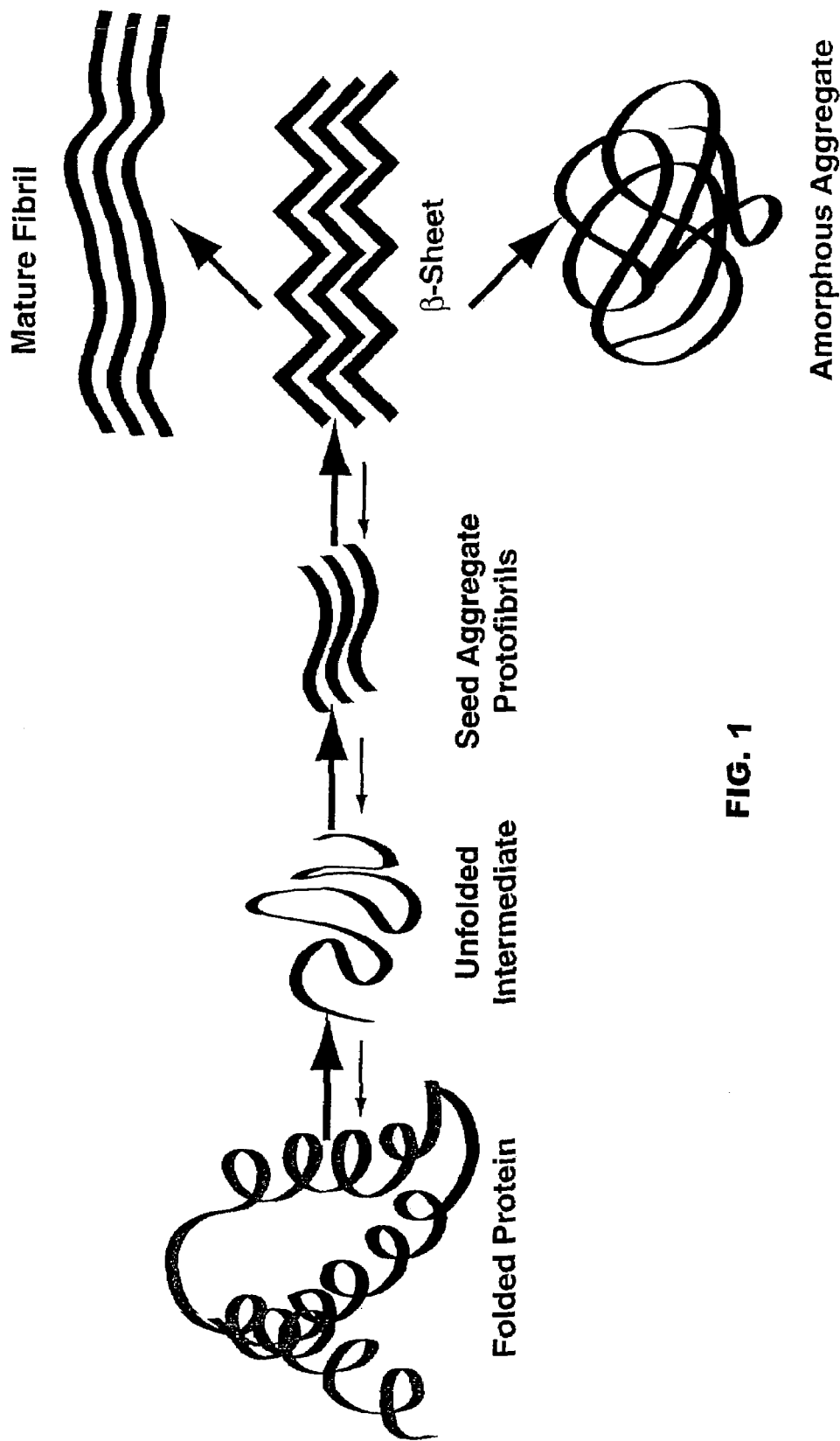
FIG. 1 is a diagram of the current model for aggregation of amyloidogenic proteins. Properly folded protein or peptide is believed to progress through a series of conversions to form a highly toxic protofibril (or seed aggregate). Protofibrils further mature into progressively more extended structures, such as fibrils and amorphous aggregates.
Figure 2:
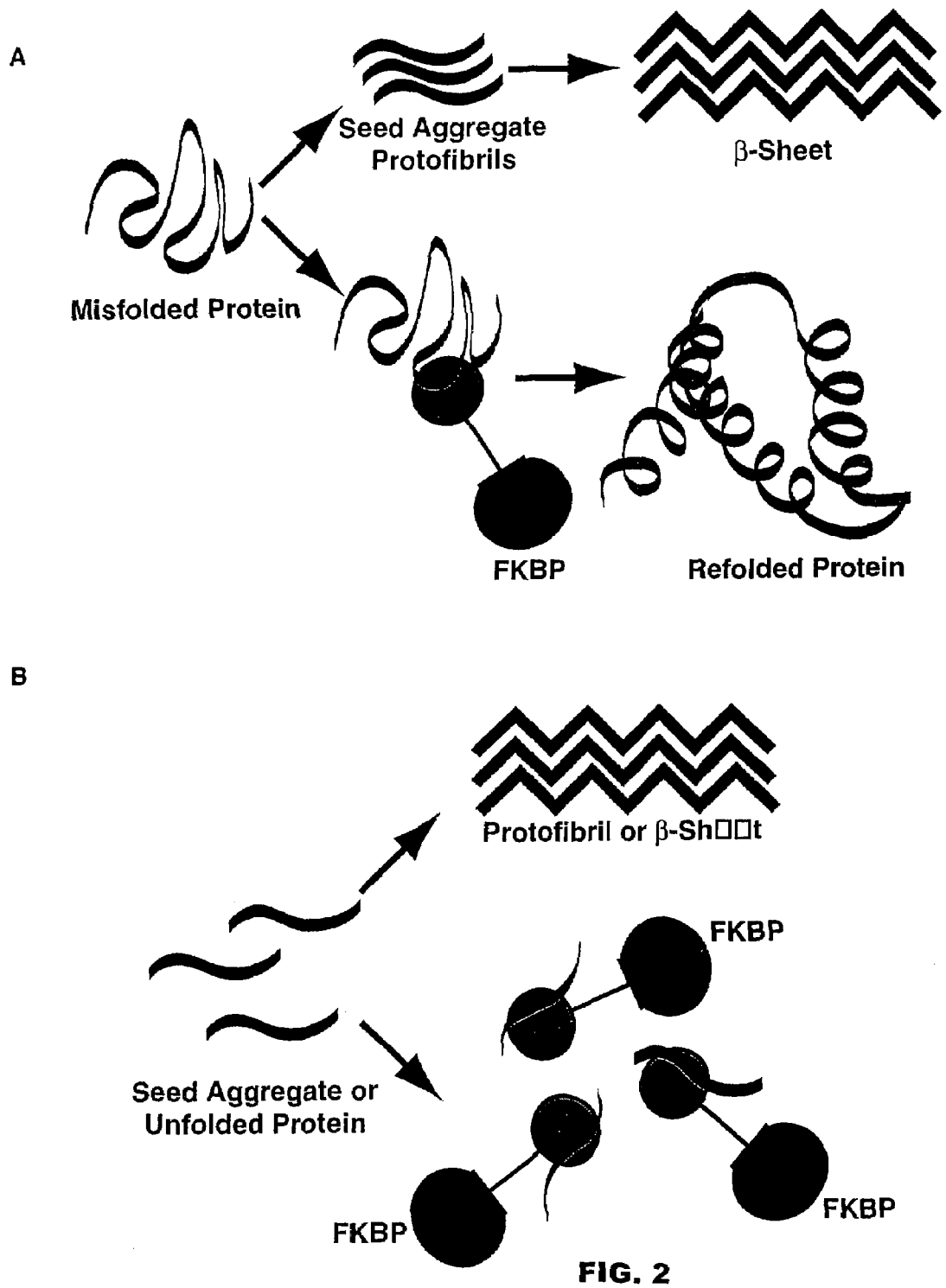
FIG. 2 is a description of two possible mechanisms by which agents could influence toxicity and/or prevent fibril formation. In the first model, the prolyl isomerase activity of FKBP, which has been recruited to an unfolding amyloidogenic peptide by the bifunctional agent, acts to lower the barrier to re-folding. In the second model, the steric bulk of the recruited FKBP prevents formation of a toxic fibrillar species.

Methods and compositions are provided for diminishing the presence of aggregates in an environment susceptible to the formation of aggregates, for example, by inhibiting protein aggregation in an environment where the formation of such aggregate is detrimental. Of particular interest is where the formation of protein aggregation is associated with neuronal pathologies. The method comprises introducing into an environment susceptible to protein aggregation a compound having a first domain or agent that functions as an aggregate binding element having an affinity for incipient or existing protein aggregations and a second independent domain or agent that serves as a recruiting element for an active factor that impedes protein aggregation. In this manner the compound recruits to the site of the protein aggregation a factor that is able to inhibit the formation of the protein aggregation and/or diminish aggregates. In the absence of the aggregation occurring, the detrimental effect or injury resulting from formation of the aggregation is avoided. Combinations of agents are preferred that can penetrate a membrane.

The compounds of this invention are complex organic compounds, usually synthetic, having one or more rings, both carbocyclic and heterocyclic, of from 10 to 120, usually of from 12 to 80 carbon atoms, more usually 12 to 60 carbon atoms, and having at least two heteroatoms and not more than about 60, usually not more than about 36 heteroatoms, more usually not more than about 30 heteroatoms, where the heteroatoms will be N, chalcogen (O or S), P, B, halogen and as cations, alkali and alkaline earth metals. The subject compounds will be in the higher molecular weight range when naturally occurring or modified naturally occurring compounds, such as the cyclosporins, are included in the molecule. Generally there will be at least 2 rings and not more than about 12 rings, usually not more than about 10 rings, where the rings will have from 3 to 8, usually 5 to 7 annular members. There may be from 1 to 4, usually 1 to 3 heteroatoms in a ring, where fused rings will usually have from 2 to 5, more usually 2 to 4 rings.

The compounds of the subject invention will for the most part have a first domain R1 that serves to bind aggregating protein molecules that are detrimental, particularly where the aggregates form injurious entities leading to neuronal pathologies; a second domain R2 that has specificity for a factor that impedes, prevents or reverses protein aggregation formation, serving to recruit the factor to an aggregate; and an entity L as a linker that serves to connect R1 and R2 to keep them together. The factor can affect the formation or dispersible of aggregates by steric hindrance to aggregate formation, modification of the components of the aggregate reducing the affinity of aggregation, or the like. R1, R2 and L will be described in seriatim.

Many compounds that bind the proteins associated with aggregation and neuronal pathologies are well known. Therefore, R1 will be such compounds as they may be modified to be linked to L and such other compounds that presently exist or may be developed in the future. In many cases R1 will have one or more functional groups that can serve as the site to bind to L. Where such opportunity does not exist, such compounds may be modified by introducing functional groups, such as —OH, —NH2 or mono-substituted —NH2, —CO2H, —CH═CH—, —C(O)CH2X, where X is halogen or pseudohalogen, etc. Such modifications will depend upon the nature of the compound, the site that permits modification without a significant adverse effect on the binding affinity of the compound, and the synthetic protocol. All of these permutations can be readily determined using combinatorial methods, if necessary. See, for example, U.S. Pat. Nos. 5,968, 736 and 6,503,759. R1 can serve as a binding agent, but may also serve in disaggregation of the aggregating monomeric proteins.

The domains of interest for R1 will for the most part be cyclic compounds, having from 1 to 8, usually 1 to 6 rings, fused or unfused, as a core structure, usually having from 2 to 6 rings, more usually 2 to 4 rings, where other rings may be present as substituents. The compounds serving as the domain will generally have at least 8 carbon atoms, usually at least about 12 carbon atoms, and at least about 1 heteroatom, usually at least about 2 heteroatoms, generally from 1 to 16, usually 1 to 12, more usually 2 to 8, heteroatoms, that are nitrogen, chalcogen (O and S), phosphorous, halogen, boron, and with acids, anions, such as the alkali and alkaline earth metals.

For the most part, the R1 domain will not exceed 60 atoms other than hydrogen, usually not more than about 36 atoms other than hydrogen and generally will not be more than 30 carbon atoms. Substituents on the core rings may be aliphatic (including alicyclic), aromatic and heterocyclic, and combinations thereof, generally of from 1 to 16, usually from 1 to 12 carbon atoms, halo, e.g. F, Cl, Br, and I, oxo-carbonyl of from 1 to 8, usually 1 to 6 carbon atoms, non-oxo-carbonyl of from 1 to 12, usually 1 to 8, more usually 1 to 6 carbon atoms, e.g. acid, ester and amide, and the nitrogen and sulfur analogs thereof, amino (including substituted amino, particularly alkyl or oxyalkyl) of from 0 to 12, usually 0 to 8, more usually 0 to 6 carbon atoms, oxy of from 0 to 8, usually 0 to 6 carbon atoms, thio of from 0 to 8, usually 0 to 6 carbon atoms, inorganic acids and their esters and amides of from 0 to 8, usually 0 to 6 carbon atoms, including sulfonic acid, sulfate, sulfenic acid, boronic acid, phosphoric acid, phosphonic acid, phosphinic acid and the nitrogen and sulfur analogs thereof, azo, nitro, cyano, etc.

The rings will generally be of from 3 to 8 annular members, more usually of from 5 to 7 annular members. Rings include benzene, furan, thiophene, azole, pyrazole, oxazole, thiazole, imidazole, pyrrole, pyrrolidine, pyrroline, piperidine, pyridine, pyrazine, pyridazine, thiazine, cycloheptane, azacycloheptane, azulene, diazacycloheptane, anthracene, etc. Various core structures include dibenzazacycloheptane, phenylpiperidine, dibenzdiazacycloheptane, dibenzdiazacyclohexane, dibenzthiazacyclohexane, dibenzthiacyclohexane, biphenyl, benzpyrrole, naphtho[2,1-b]furan, naphthacene, anthracene, stilbene, etc.

Compounds of interest include: 1-Br or I-2,5-bis(3-hydroxycarbonyl-4-hydroxy)stilbene, thioflavin, thioflavin T, chrysamine G, X-34, Congo red, IMPY (Kung, et al., 2002 Brain Res 956, 201-10), imipramine, carbamazepine, phenazine, phenothiazine, promazine, chlorpromazine, haloperidol, clozapine, 2-chlorophenothiazine, promethazine, chlorprothixen, acepromazine, deoxydoxorubicin, rifamycin, acridone and acridone derivatives, such as flavinoids and alkaloids, benzofurans, such as 5-(3-(4-(2-methoxyphenyl)-1-piperazinyl)propionyl)benzofuran (He, et al., 2002 Chinese Chem J on Internet 4, 13), and benzofurane (SKF74652), quinacrine and other 9-substituted acridines, e.g. 1-(3-dimethylaminopropyl-1-amino)4-nitro-7-methylthio-9-acridone, pamaquine, chloroquine and amacrine, methylene blue, and the like.

The disaggregation protein binding compound can be any protein that interferes with aggregation formation by steric hindrance, enzymatic activity or other mechanism. By virtue of an incipient or formed aggregation having a plurality of members and an extended surface, a plurality of the first domain may bind to the aggregation. In this way, multiple target proteins may be recruited to the site of the aggregation to act on the aggregation. As discussed previously, the subject compounds allow for the recruitment of various protein agents to inhibit or modify incipient or formed aggregations. Of particular interest in vivo as the second domain, R2, is an agent that serves to recruit a prolyl isomerase. R2 may bind to any epitope of the recruited protein, for an enzyme including the active site of the enzyme. The binding will usually be reversible, particularly where the binding compound binds at the active site.

The prolyl isomerase enzyme will be classified as EC.5.2.1.8 and may be one of the human genes related to FKBP or cyclophilin, Pin1, hParv14, etc. The binding domain will bind to at least the human enzyme and may bind to enzymes of other species. These domains will in many situations be based on naturally occurring compounds and may therefore be relatively large. The domains will generally have from about 10 to 80 carbon atoms and from about 2 to 30, usually 6 to 24 heteroatoms, where the heteroatoms will be N, chalcogen (O or S), P, B, halogen and as cations, alkali and alkaline earth metals. The functional groups listed for R1 will also be applicable for R2. Compounds of interest to serve as domains include FK506, rapamycin and derivatives thereof, cyclosporinA and modified cyclosporins (See, U.S. Pat. No. 6,444,643), 18-OH-ascomycin (Mollison, et al., 1997 J Pharmacol Exp Ther 283, 1509-19), sanglifehrin A derivatives (Zenke, et al., 2001 J Immunol 166, 7165-71), KLVFF, and the like. Other proteins may be recruited that will discourage aggregation, particularly of the individual neurodegenerative proteins. These proteins include the heat shock proteins, e.g. hsp70 and hsp90 that serve as chaperonins, or other chaperonins, where the heat shock proteins can be recruited by geldenamycin.

The two domains are joined by a linking group L that may only be a bond or have not more than about 20 atoms in the chain, usually not more than about 12 atoms in the chain. It should be understood that the functional group associated with the domain for binding to the linker is not included in the counting of the atoms of the chain. For cyclic compounds the shortest path will be counted. Depending on the nature of the two domains, different linking groups may provide for optimization of the activity of the product. The linkers can provide spacing between the two domains, rigidity or flexibility between the two domains, hydrophilicity or hydrophobicity, hydrogen bonding, etc. Thus, the examples given in the Experimental section provide guidance as to the effect of the linking group with the particular domains that are employed.

The total number of atoms other than hydrogen for the linking group will not exceed about 36 atoms, usually not more than 20 atoms, more usually not more than 16 atoms, frequently not more than about 12 atoms. The chain may be aliphatic (including alicyclic), aromatic or heterocyclic, or combinations thereof, saturated or unsaturated, where heteroatoms will be N, chalcogen, or P, including such functionalities as oxy, ester, amide and the nitrogen and sulfur analogs thereof, amino, substituted amino, inorganic acids, particularly phosphorous acids. e.g. phosphate, thio, oxo, halo, etc. Where rigidity of the linking group is desired, of particular interest is the inclusion of an aromatic group in the chain, particularly a carbocyclic aromatic group, of from 5, usually 6 to 12 carbon atoms, where heteroannular atoms will for the most part be N, O and S. Alternatively, one may use ethylenic or acetylenic unsaturation to provide for the rigidity. The linking group may serve solely to join R1 and R2 without significantly affecting the characteristics of the compound or may provide for solubility, enhanced membrane penetration, stability, pharmacological distribution, excretion, and reduction in toxicity or other desired characteristic.

The linking group will be selected in light of the two domains being linked, the available functionalities for linking, the presence of functionalities that must be protected and deprotected, the effect on the properties of the final product, and the like. Illustrative linking groups include a bond, amino, methylamino, succinoyl, maleoyl, pimeloyl, ethylenediamino, glycine, 1,3-dihydroxypropylene, phenylenediamine, p-aminobenzoic acid, glycinamido 4-aminobutyric acid, bis (2-hydroxyethyl) phosphate, di(amino acids), such as glycylglycine, tryptophanylalanine, methionylvaline, etc., ω-amino-aliphatic acids of from 3 to 10, usually 3 to 6, carbon atoms, oxyalkylamino substituted aliphatic acids of from 2 to 10, usually 2 to 6, carbon atoms, such as 2'-aminoethoxy-3-propionic acid, 3'-aminopropoxyethoxycrotonic acid, etc.

Figure 3:
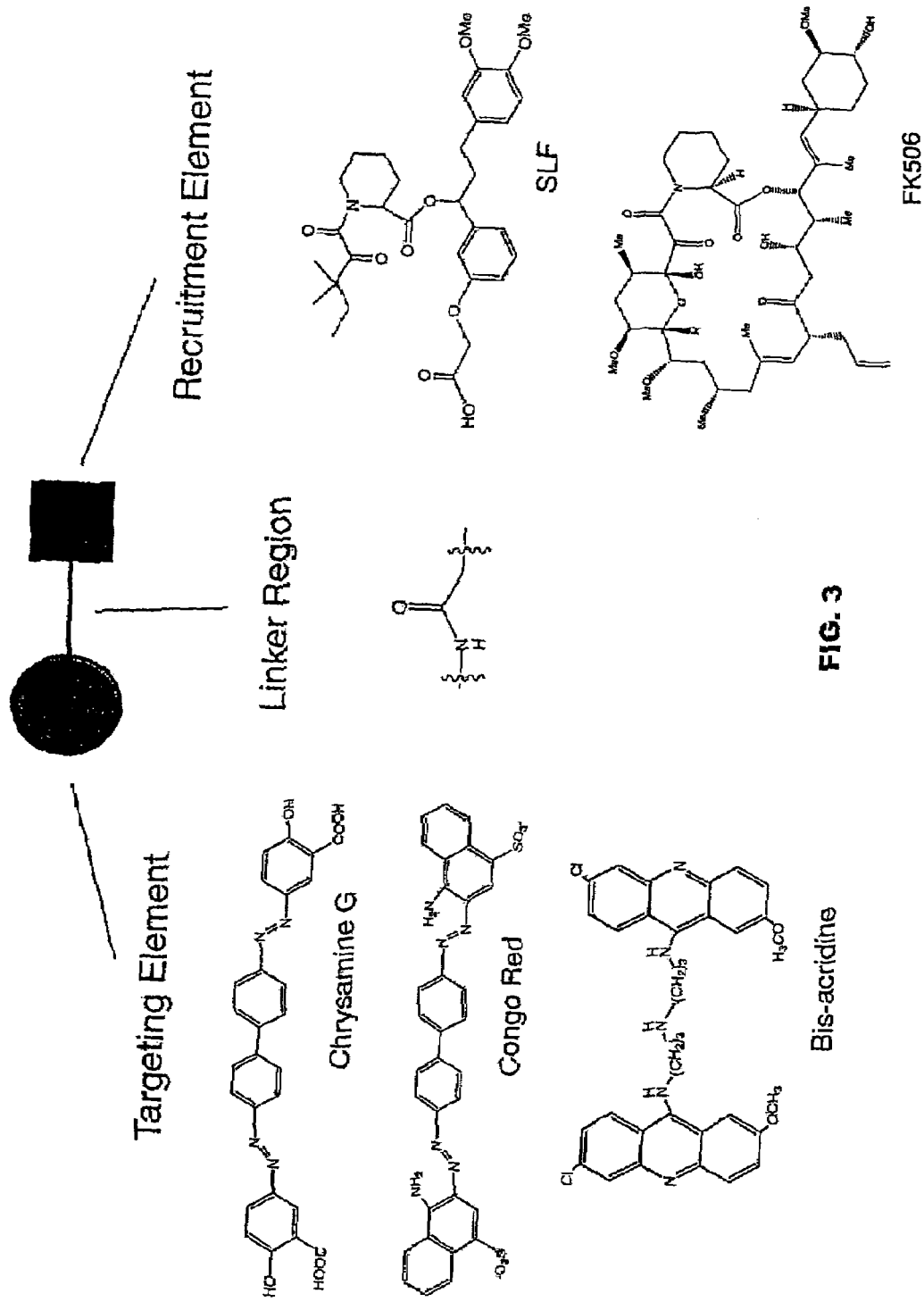
FIG. 3 is a diagram of the agents of this invention.
Figure 4:
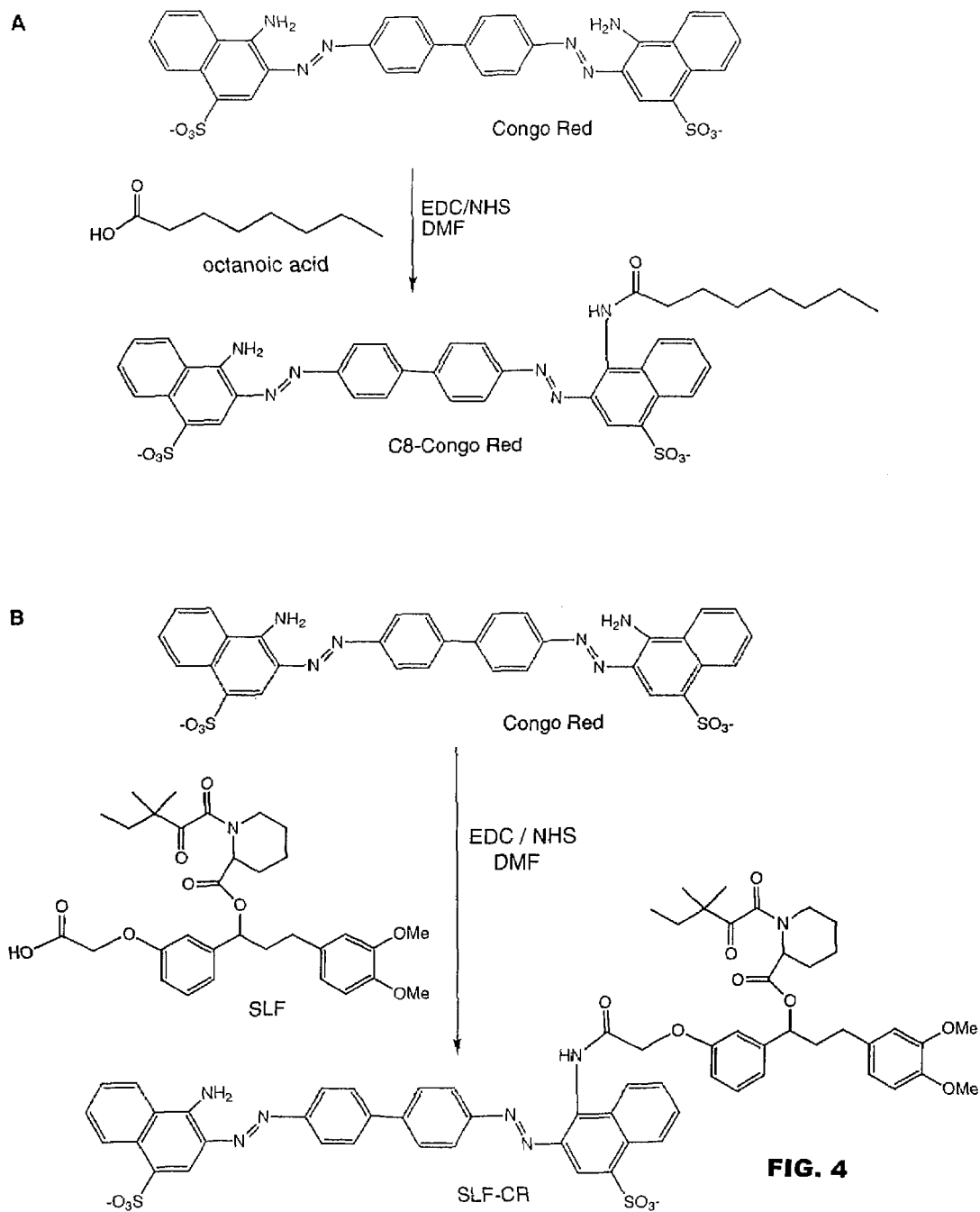
FIG. 4 is a diagram of the synthesis of the agents of this invention.
Figure 5:
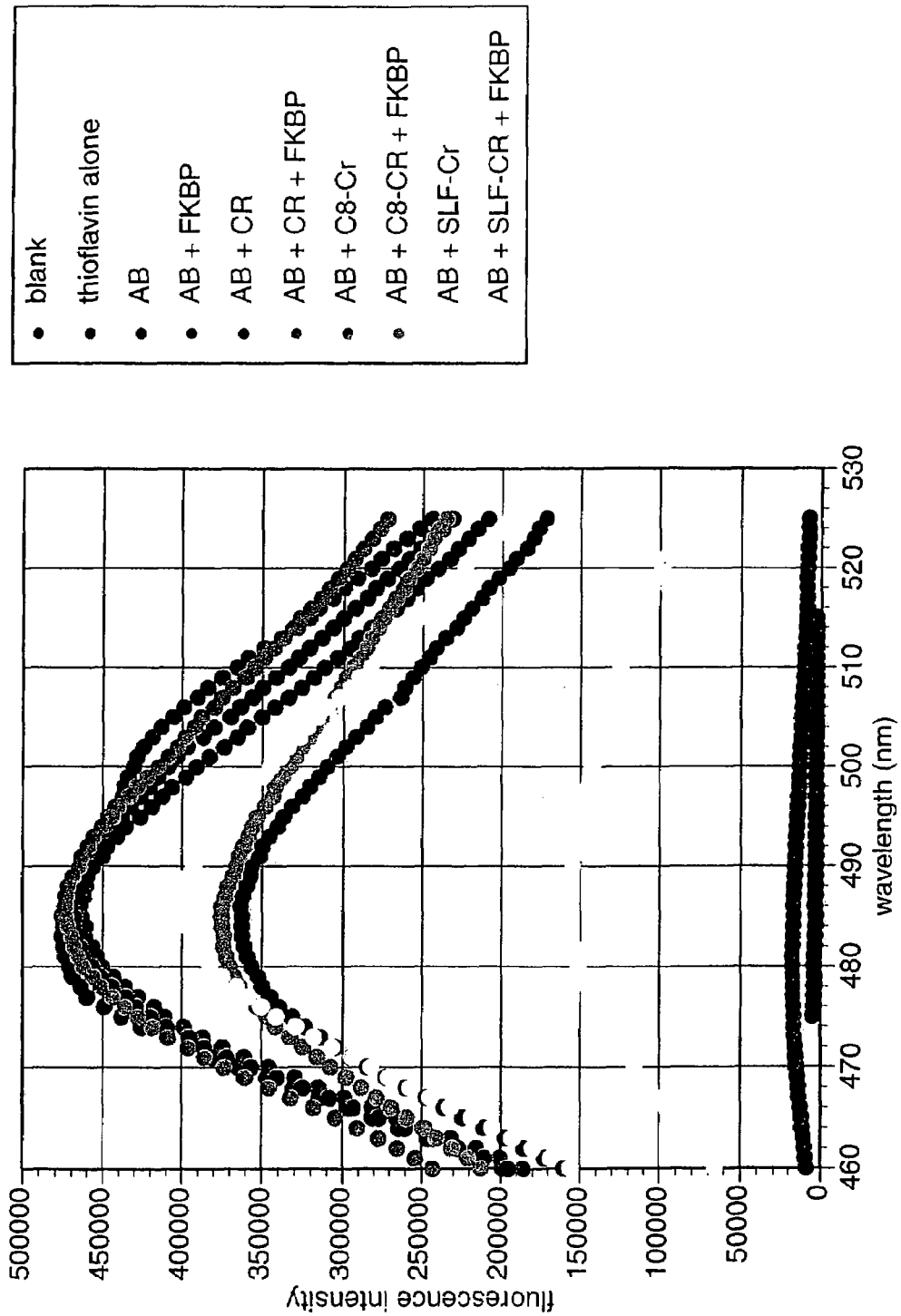
FIG. 5 is a graph of the observed fluorescence with the Thioflavin T assay under the conditions outlined in the Experimental section. The graph shows that fibril formation is inhibited by addition of a combination of SLF-CR and FKBP12.
Figure 6:
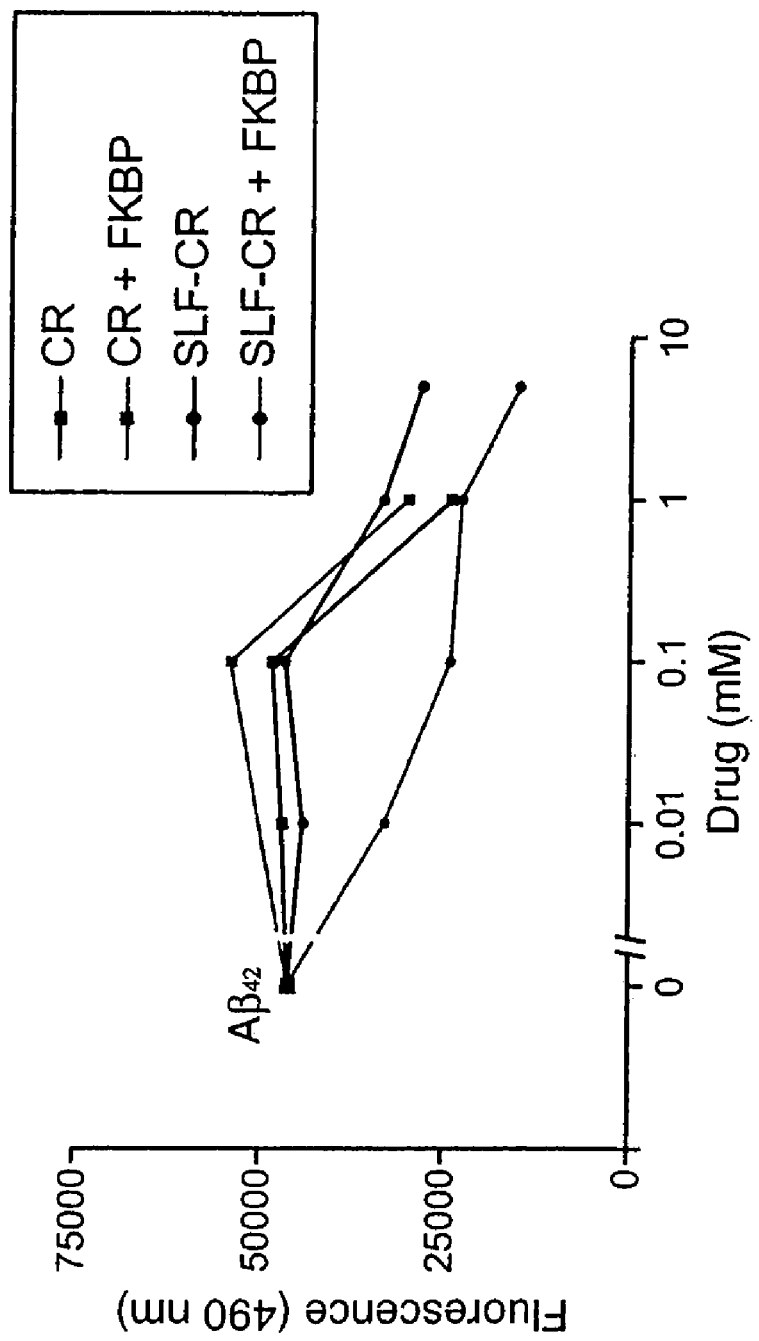
FIG. 6 is a graph showing the effect of varying the concentration of an agent of this invention on fibril formation using the Thioflavin T assay. The concentration of FKBP, which was present during the fibrillization procedure, was held constant at 1 µM.
Figure 7:
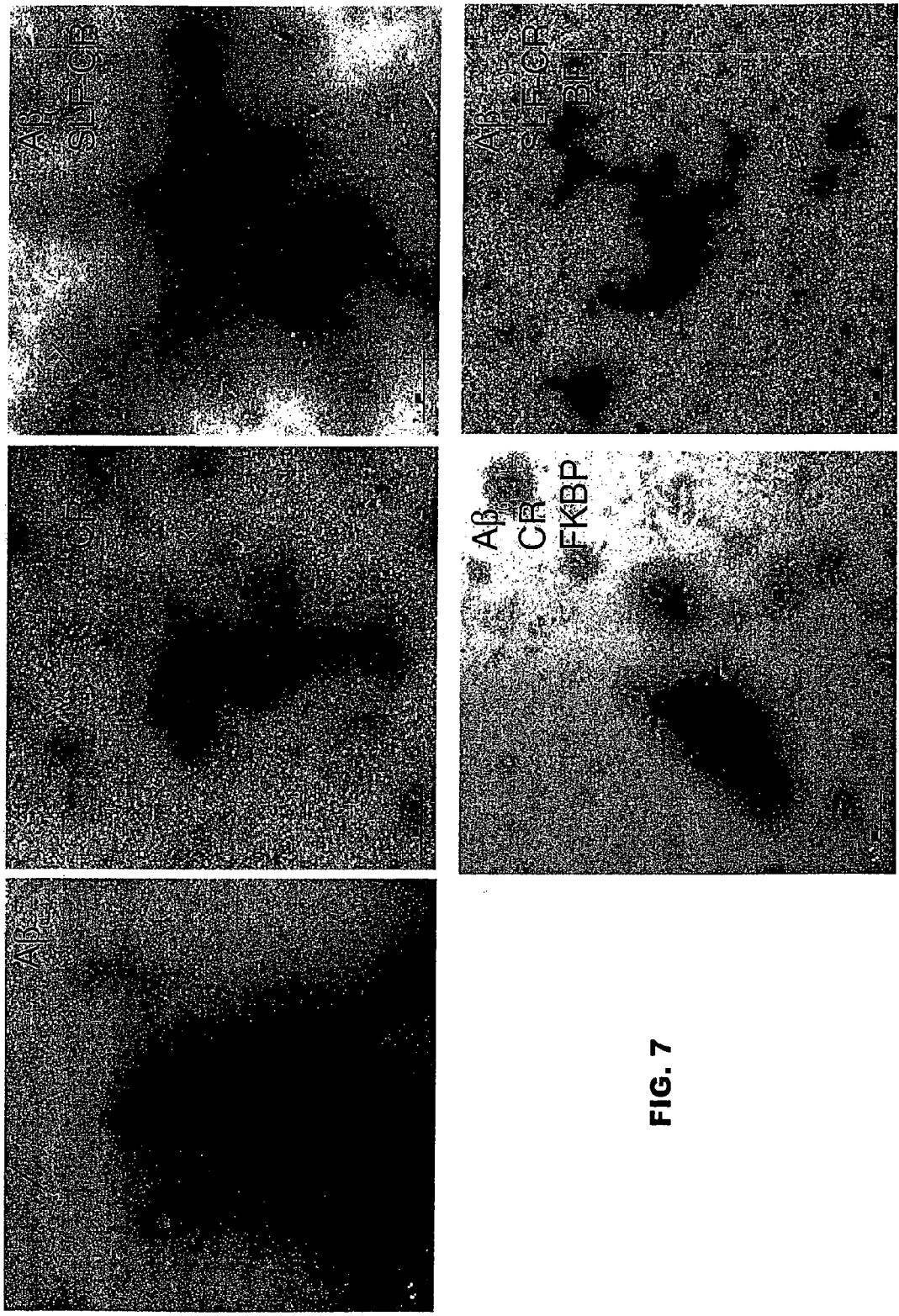
FIG. 7 is a series of TEM images that demonstrate the disruption of fibril formation by an agent of this invention when FKBP is added. Representative fibrils have been outlined with dotted lines and highlighted by arrows. The fibrils formed in the presence of a combination of SLF-CR and FKBP are clearly less abundant and generally smaller. TEM was performed as outlined in the Experimental section.
Figure 8:
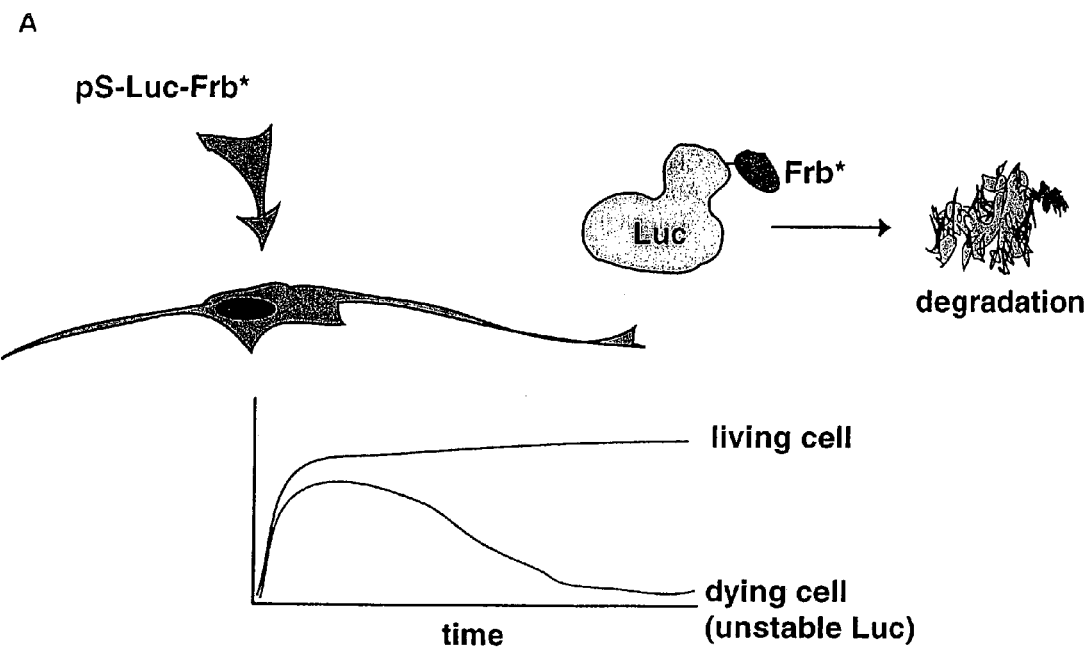
FIG. 8 is a diagram and graph describing the luciferase assay and the results obtained from this assay. Panel A is a diagram of the assay procedure. Panel B is a graph that demonstrates that an agent of this invention can prevent toxicity of aggregated amyloidogenic peptide. Further, this inhibition of toxicity is greatly enhanced by the presence of FKBP.
Figure 8:
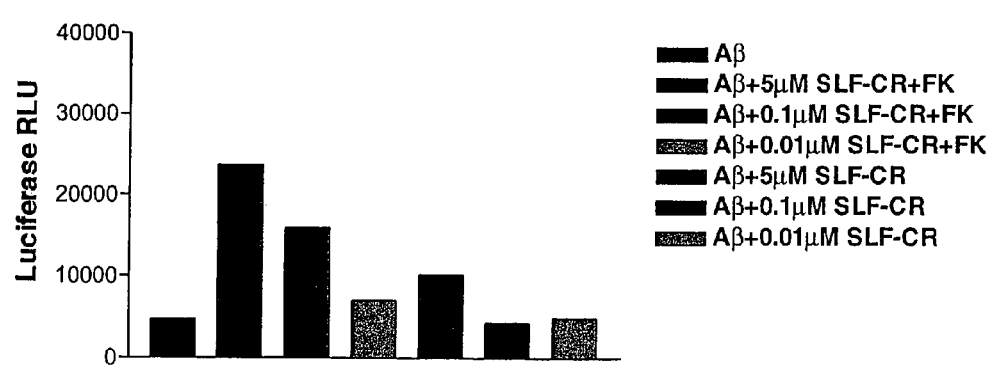
Figure 9:
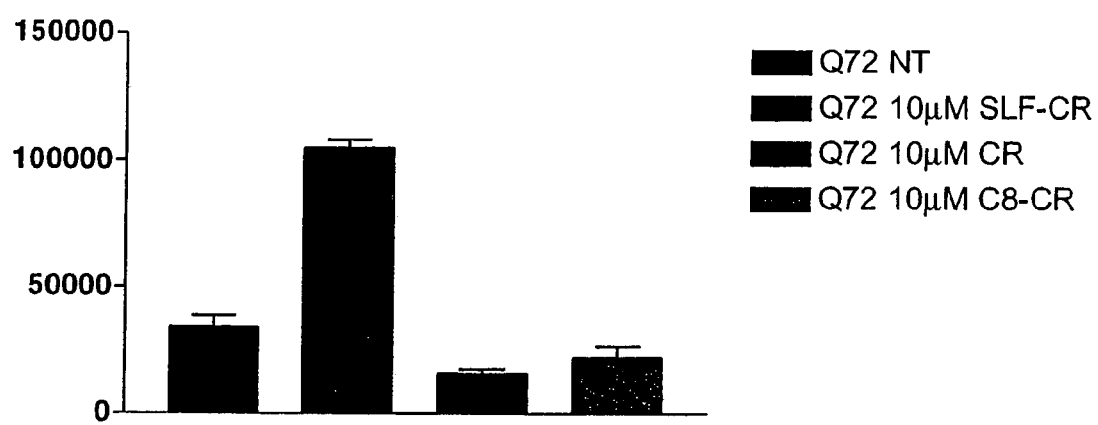
FIG. 9 is a graph of data from the luciferase assay showing that addition of an agent of this invention can promote survival of primary neurons transfected with the Q72 form of Huntingtin amyloidogenic protein.

See, FIG. 3, where a number of compounds are indicated, with a targeting element for binding to the neurodegenerative proteins and a recruitment element for binding to the prolyl isomerase. The domains can be derived from compounds that are known and have been shown to be physiologically benign. Using these known compounds to provide the domains allows for the ready preparation of compounds that will have physiologically acceptable properties.

The compounds will be synthesized in accordance with known protocols and reactions. Methods for modifying the various domain compounds are well known in the literature and can be used successfully, if necessary, to introduce functionalities, when required. See, for example, U.S. Pat. No. 6,372,712.

A number of in vitro (including cultures) and in vivo tests are known for evaluating activity of compounds in reversing aggregation of the neurodegenerative proteins. In vitro studies include transient transfection of cells (Dou, et al., 2003 PNAS 100, 721-6) with tau gene, use of anti-phosphorylated tau in an immunoassay (Lu, et al., supra), surface plasmon resonance assay (Cairo, et al., supra), cellular toxicity with PC-12 cells (Lowe, et al., supra), and ThT fluorescence spectroscopy (Ghanta, et al., supra). Mouse models are described in Lee, supra, references cited in Goedert, supra, references cited in Lee, et al., supra, and references cited in Zoghbi and Orr, supra.

The subject compounds find use in investigating the etiology of the different neurodegenerative diseases, the response of the diseases to various compounds in conjunction with the subject compounds, that substantially reduce the level of aggregation of the individual proteins, and the response of the neurodegenerative proteins to various proteins that are recruited by the subject compounds to the aggregate. The subject compounds may also be used with naturally occurring or synthetic compounds to evaluate their propensity to induce aggregation formation. Where a prolyl isomerase is recruited, one can investigate the effect of the modification of the geometry of the proline on the stability of the aggregates and the response to other drugs at a reduced level of aggregation.

By using the subject protocols with conjugates having a first domain binding to the neurodegenerative proteins, particularly in their β-sheet conformation, and a second domain that recruits proteins, such as prolyl isomerases, one can evaluate other drugs that affect the formation of the aggregates and the neurotoxicity of such aggregates. One can also evaluate the effect on the aggregate formation, as to time, fibril formation and aggregate formation. In addition, one can use the subject compounds to screen for other compounds that bind the aggregates, evaluating the effect of the binding of such compounds on aggregate formation and neurotoxicity. By using standardized tests, one can determine the binding affinity of test compounds and their effect on aggregation by providing a competition between an agent of the subject invention, which can also serve as a standard, and such test compound. By testing in the presence and absence of a prolyl isomerase, and measuring the effect on aggregation and neurotoxicity, the effect of the test compound on these two indications can be determined.

In addition, the subject compounds can find use in the treatment of neurodegenerative disorders, based on protein aggregation. The subject compounds will generally have an IC50 of less than about 10 uM, preferably less than about 1 uM and more preferably less than about 50 nM. The subject compounds are capable of being administered orally, by injection, parenterally, intravascularly, intraperitoneally, intracranially, subcutaneously, etc. Dosages will vary widely depending upon the mode of administration, the activity of the subject compound, the status of the patient, whether the subject compound is being administered prophylactically or therapeutically, the frequency of administration, the response of the patient to the drug and dosage, the rate of distribution, excretion, metabolism and ability to cross the blood brain barrier.

Administration may be by continuous infusion, slow release formulations, a pump, bolus, etc. The administration may be daily or more or less frequently, generally not less than about 1 time a week, when the patient is under therapy. The dosage will be an effective dosage administered in accordance with its effectiveness to achieve the level of response desired from the patient, while protecting the patient from detrimental side effects. Generally the daily dosage will be less than 500 mg, usually less than about 100 mg, and preferably less than about 1 mg. Usually, the daily dosage will be greater than about 0.01 mg. The dose will be regulated to provide a blood level at a prophylactically or therapeutically effective amount.

The subject compounds can be formulated in accordance with known formulation techniques and compositions. These compositions will include a prophylactically or therapeutically effective amount of the active compound and a pharmaceutically acceptable carrier, which may include a variety of additives as part of the carrier. As used herein, the phrase "pharmaceutically acceptable carrier" intends a non-toxic, usually inert, solid, semi-solid, or liquid filler, diluent, encapsulating material, formulation, auxiliary of any type, including a sterile aqueous medium, saline, etc.

Exemplary of such materials are sugars, such as lactose, glucose and sucrose, starches, such as corn starch and potato starch, cellulose and modified cellulose, such as sodium carboxymethylcellulose, hydroxyethylcellulose, ethyl cellulose, cellulose acetate, etc., powdered tragacanth, malt, gelatin, talc; excipients, such as cocoa butter and suppository waxes, oils, such as peanut oil, cottonseed oil, safflower oil, sesame oil, olive oil, corn oil, and soybean oil, polyols, such as propylene glycol, glycerin, sorbitol, mannitol and polyethylene glycol, esters such as ethyl oleate and ethyl laurate, agar, buffering agents, such as magnesium and aluminum hydroxide, and phosphate buffered saline, alginic acid, Ringer's solution, ethyl alcohol, etc.

Wetting agents, emulsifiers and lubricants, such as sodium lauryl sulfate and magnesium stearate, as well as coloring agents, releasing agents, coating agents, sweetening agents, flavoring agents, perfuming agents, preservatives and antioxidants may also be included in the formulations. Examples of pharmaceutically acceptable antioxidants include, but are not limited to, water soluble antioxidants, such as ascorbic acid, cysteine hydrochloride, sodium bisulfite, sodium metabisulfite, sodium sulfite, etc.; oil soluble antioxidants, such as ascorbyl palmitate, butylated hydroxyanisole, butylated hydroxytoluene, lecithin, propyl gallate, alpha-tocopherol, etc.; and the metal chelating agents, such as citric acid, ethylenediamine tetraacetic acid, sorbitol, tartaric acid, phosphoric acid, etc.

Liquid formulations for oral administration will include pharmaceutically acceptable solutions, emulsions, microemulsions, suspensions, syrups and elixirs, employing the agents described previously.

Injectable formulations may be solutions or suspensions, employing media described previously, such as water, Ringer's solution, isotonic saline, bland fixed oils, such as mono- or diglycerides, and may include fatty acids, e.g. oleic acid.

Depots of the drug may be employed with subcutaneous or intramuscular injection. The injection will usually be a slow release suspension of crystalline or amorphous material, where the rate of dissolution of the suspension and/or transport of the drug to the surface of the particles will determine the release rate of the drug. Alternatively microencapsulation may be employed employing biodegradable polymers, e.g. polylactide-polyglycolide, polyorthoesters, and polyanhydrides.

Solid dosage forms for oral administration may include capsules, tablets, pills, powders, gelcaps, and granules. The active ingredient is mixed with at least one inert diluent, such as sucrose, lactose or starch. Other components may include tableting lubricants, extenders, release controlling coatings, etc. Soft- or hard-filled gelatin capsules may be employed, using such excipients as lactose or milk sugar, high molecular weight polyethylene glycols, and the like.

In some instances transdermal administration may be effective. Appropriate additives are provided for transferring the subject compounds across the skin and into the blood stream. Inhalation may also be used, where an aerosol of the active ingredient is employed and the active ingredient crosses the lung membrane.

The compositions of the subject invention may be administered as the only active ingredient or in combination with other compounds, such as dopamine, antiinflammatory agents, enzyme inhibitors, blood brain barrier permeabilizing agents, and the like.

The subject compounds can be used in vivo or in vitro to inhibit aggregation in environments or compositions that result in aggregation by enhancing localized concentrations of enzymes that interact with the aggregation. As described above, in in vivo situations, one can administer a compound according to this invention that will bind to an aggregate and recruit the enzymes to the site. In lysates or other complex mixture, particularly having a variety of proteins, one can determine what domains may be used to prevent one or more components of the mixture to form an aggregate. Where the binding of the target domain is known, one can enjoy the benefit of an endogenous protein or add the protein, if necessary. In this way, where aggregation of components of a mixture to be analyzed will interfere with the analysis, by adding a compound according to this invention, the binding of the compound to aggregate forming components at an early stage of aggregation and recruitment of a target protein to the site of aggregation can inhibit the formation of the aggregate.

For recruiting enzymes, one may use substrate or co-enzyme mimics, compounds that bind to epitopes or other feature of the enzyme, etc. Mimics may include for kinases AMP, γ-S ATP, etc., for phosphatases, phosporamide, thiophosphate, thiophosphoramide, etc., for proteases, amine substitutes for carboxamide, and compounds that bind to enzymes, such as SLF to prolyl isomerases, etc. By recruiting enzymes that can modify the monomers of the aggregate, aggregation may be impeded or the monomers dispersed.

The following examples are intended to illustrate but not limit the invention.

EXPERIMENTAL

Synthesis of C8-Congo Red. Agents of this invention were synthesized using standard chemical procedures. EDC (13.7 mg; 0.0885 mmole; 5 eq), sulfo-NHS (20.6 mg; 0.0885 mmole; 5 eq), and octanoic acid (2.55 uL; 0.0177 mmole; 1 equivalent) were dissolved in 100 uL dimethyl furane (DMF). After stirring for 10 minutes at room temperature, Congo red (16.8 mg; 0.0345 mmole; 2 equivalents) was added in 100 uL of DMF. This mixture was stirred at room temperature and monitored by thin layer chromatography (TLC) on silica gel plates. After 60 minutes, the reaction was brought up in methanol: ethyl acetate (10:90) and subjected to purification by silica gel chromatography. Fractions were analyzed by TLC and UV-visible spectroscopy. Pooled fractions were dried and a sample analyzed by mass spectrometry.

Synthesis of SLF-Congo Red. EDC (13.7 mg; 0.0885 mmole; 5 eq), sulfo-NHS (20.6 mg; 0.0885 mmole; 5 eq), and SLF (10 mg; 0.0177 mmole; 8.8 mM final) were dissolved in 100 uL DMF. After stirring for 10 minutes at room temperature, Congo red (16.8 mg; 0.0345 mmole; 2 equivalents) was added in 100 uL of DMF. This mixture was stirred at room temperature and monitored by TLC on silica gel plates. After 60 minutes, the reaction was brought up in methanol:ethyl acetate (10:90) and subjected to purification by silica gel chromatography. Fractions were analyzed by TLC and UV-visible spectroscopy. Pooled fractions were dried and a sample analyzed by mass spectrometry.

Fibrillization Procedure. Purified amyloid beta (1-42) was purchased from AnaSpec and used without further purification. Fibrillization conditions are based on those previously described by Gordon and Meredith (Gordon, D. J. and Meredith, S. C. (2003) Biochemistry 42:475-485). Briefly, peptide was dissolved in PBS to a final concentration of 100 uM. To this solution, was added either FKBP12 (to a final concentration of 1 uM) or an equivalent volume of buffer alone (100 mM NaCl, 10 mM Tris-HCl pH 7.0). Additionally, either agent (dissolved in DMF) or DMF alone was added. These mixtures were placed at room temperature for at least 4 days without disruption.

Thioflavin T assay. Assay conditions were based on those previously described (Gordon, D. J. and Meredith, S. C. (2003) Biochemistry 42:475-485). Briefly, a 5 uL solution, which was derived from the fibrillization procedure above, was added to 200 uL of 5 uM thioflavin T in 50 mM glycine buffer pH 8.5. The mixture was vortexed briefly and the fluorescence emission maximum measured. For the dose dependence experiment, the emission wavelength was recorded at 490 nm. Excitation was set at 446 nm.

Transmission Electron Microscopy (TEM). Electron microscopy was performed essentially as previously described (Gordon, D. J. and Meredith, S. C. (2003) Biochemistry 42:475-485). Briefly, solutions subjected to the fibrillization conditions described above were applied to Formvar coated 400-mesh glow-discharged copper grids and contrasted with 1% uranyl acetate solution. Grids were analyzed at 80 kV and a magnification of 100,000×.

Luciferase assay. Neuronal culturing, transfection with plasmid DNA, and luciferase assays were performed as previously described (Graef et al 1999, supra).

Surface Plasmon Resonance. Amide coupling was used to generate a carboxymethyldextran (CM5; BIAcore, Uppsala, Sweden) sensor chip bearing a mockimmobilized surface on flow chamber 1 (Fc1), 950 RU of Aβ(1-40) (AnaSpec, San Jose, Calif.) on Fc2, and 2800 RU of bacterially-expressed recombinant FKBP12 on Fc3. The regeneration conditions were as follows: for removing analyte from Aβ surfaces (4 M guanidine HCl, 10 mM Tris buffer pH 8.0) and for removing analyte from the FKBP surface (750 mM NaCl, 250 mM NaOH). To calculate $K_{D1}$ and $K_{D2}$ (±SEM) for Aβ binding (in part C), the control signal was subtracted and data was fit according to the method of Cairo et al. (*Biochemistry* 41, 8620-8629 (2002).

In each case, eight concentrations of analyte distributed around the $K_D$ were injected in duplicate in the running buffer (HBS-EP; BIAcore). Congo red is not uniquely specific for Aβ and, consistent with this, it also binds FKBP, but at a $K_D$ 20-fold higher than SLF-CR.

Light Scattering. Fresh Aβ(1-42) (Anaspec, San Jose, Calif.) was prepared by resuspending the peptide in 100 mM NaOH pH 9.5 to 10, sonicating for 5 minutes, and passing the resulting solutions through a 10 kDa filter (YM-10; Millipore, Bedford, Mass.) (31). Stock solutions (100 μM in 2 mM NaOH) were stored at −80° C. and diluted to 25 uM with PBS pH 7.2 to initiate fibrillogenesis. Identical methods were used to prepare the Aβ(1-42) solutions utilized for TEM, AFM, MTT, Tunel and thioflavin T experiments. Turbidity was measured at 30° C. with orbital shaking in half area, nonbinding surface 96-well plates (Corning) on a TECAN GENios plate reader. The total volume was 50 uL and the concentration of FKBP was 1 uM. The results are representative of two independent experiments each performed in triplicate.

Thioflavin T. Compounds (CR or SLF-CR), FKBP (1 uM), and Aβ (25 uM) were incubated in a total volume of 10 μL PBS pH 7.2 in black Corning 96-well plates. After a 96 hour incubation in the dark at 22° C., thioflavin T (200 uL of 5 μM thioflavin T in 50 mM glycine pH 8.5) was added. Fluorescence was measured on a SpectraMax Gemini (Molecular Devices, Sunnyvale, Calif.), using an excitation wavelength of 446 nm (±5 nm) and an emission of 490 nm (±5 nm). The data was fit to sigmoidal curves using DeltaGraph (DeltaPoint, Inc) and the $IC_{50}$ for each treatment recorded. The percent aggregation is arbitrarily defined as 0% by the fluorescence of a solution of thioflavin T to which no Aβ has been added ($Em_{490\ nm}$=3.3) and for 100% by the fluorescence of a solution containing Aβ but no inhibitors ($Em_{490\ nm}$=42). A linear relationship between thioflavin T fluorescence and percent aggregation was used for simplicity.

Transmission Electron Microscopy. TEM was conducted using 300 mesh formvar-coated copper grids and 1% uranyl acetate stain on a JEOL TEM1230 and imaged with a Gatan 967 slow-scan CCD at 80 kV. Samples were incubated for 4 days at 22° C. in PBS pH 7.2 containing 25 uM Aβ(1-42), 1 μM FKBP and 1 uM drug, where appropriate. The protocol used to prepare Aβ can influence fibrillogenesis and the reproducibility of the assays. Therefore, it can be useful to examine Aβ aggregation under a variety of conditions. In addition to the hydroxide method used above, stock solutions of Aβ were also prepared using a trifluoroacetic acid (TFA) protocol (Crystal, et al., *J. Neurochem.* 86, 1359-1368 (2003). TEM on samples originated from these stock solutions yielded similar results, although the typical size of the fibrils was considerably shorter.

Atomic Force Microscopy. Samples for AFM were prepared as for TEM, above, applied to a clean silicon surface, washed twice with $dH_2O$, dried, and imaged at a scan rate of 1 Hz using a silicon probe (TESP) on an AFM Nanoscope Dimension 3000 (Digital Instruments) in Tapping Mode (C. Goldsbury, et al, *J. Mol. Biol.* 285, 33-39 (1999). The dimensions of the globular aggregates in the samples treated with SLF-CR/FKBP were approximated using NIH Image.

Cell Viability Assay. Rat hippocampal (E19.5 and P0) neurons were prepared as previously described (Graef, et al., *Nature* 401, 703-708 (1999). Fresh Aβ(1-42) (100 uM) was prepared under basic conditions and incubated with inhibitors for two days at 22° C. in PBS pH 7.2 and then diluted 1:4 with culture media and applied to neurons. MTT assays were conducted as per manufacturer's specifications after two additional days of incubation at 37° C. and 5% $CO_2$. The inhibitor concentrations are the in vitro incubation values.

Immunofluorescence Microscopy. Rat hippocampal neurons (P0) were cultured 10 days on Matrigel-coated glass coverslips (Deckgläser, Germany) in 24-well plates (Corning) at 37° C. and 5% $CO_2$. Aβ solutions were prepared and applied as above. The final concentration of Aβ was 25 uM and drug and FKBP were present at 1 uM. Following a two-day incubation, cells were prepared for microscopy as described (R. Kayed, et al., *Science* 300, 486-489 (2003).

The results from the assays indicated above are as follows:

Results

As a first measure of SLF-CR function, we examined the binding of the compound to immobilized Aβ(1-40) by surface plasmon resonance. We found that the affinity of SLF-CR for Aβ is not significantly different from that of CR, which suggests that the conjugation of SLF to Congo red does not dramatically interfere with binding. Similarly, unmodified SLF and SLF-CR bind immobilized FKBP with comparable affinity. These results confirmed that the targeting and recruiting domains of SLF-CR retain affinity for their respective targets.

To test the capacity of SLF-CR to simultaneously bind Aβ and FKBP, the bifunctional compound was pre-incubated with FKBP and the resulting solutions passed over immobilized amyloid. In surface plasmon resonance, the response (in arbitrary units, RUs) is proportional to the mass of material assembled on the surface. We used this characteristic to determine whether SLF-CR could form a ternary complex with FKBP and immobilized Aβ. Consistent with this model, the combination of SLF-CR and FKBP gave a greater response (~230 RUs) than SLF-CR alone (~140 RUs). While interpretations of the efficiency of complex formation are prevented by a lack of detailed information regarding the binding site(s) of Congo red on Aβ, this result suggests that SLF-CR can trigger formation of the FKBP/drug/Aβ ternary complex. Recruitment of FKBP to Aβ by SLF-CR, but not CR, was also confirmed by electron microscopy.

To assess the impact of chaperone recruitment on the potency of aggregation inhibitors, the aggregation-prone 42-amino acid version of Aβ (Aβ(1-42)) was incubated in the presence of drug and FKBP. Aβ fibrils scatter light; therefore, the turbidity of Aβ solutions can be used to follow fibrillogenesis in real time. These experiments revealed that SLF-CR/FKBP at 10 uM completely blocked the formation of Aβ aggregates capable of scattering light. Full inhibition by SLF-CR required FKBP, but FKBP alone did not interfere with Aβ aggregation. CR was a modest inhibitor of turbidity and FKBP was unable to significantly alter its potency. Even at nanomolar concentrations, SLF-CR/FKBP ($IC_{50SLF-CR}$ 0.43 uM) delayed amyloid aggregation.

As a second measure of inhibition, we explored the aggregation of Aβ by the well-established thioflavin T assay. The fluorescence of thioflavin T at 490 nm dramatically increases in the presence of Aβ aggregates, which makes this an attractive assay for screening inhibitors. Similar to the results obtained by light scattering measurements, we found that the $IC_{50}$ of SLF-CR/FKBP was approximately 5-fold lower than that of CR/FKBP for lowering the concentration of thioflavin-T-binding species. Moreover, at 10 uM drug, only the combination of SLF-CR and FKBP was capable of completely preventing thioflavin T reactivity (i.e. the fluorescence of the sample is equivalent to that of Aβ-free solutions of thioflavin T). Between 20 and 35% of aggregates remained after similar treatment (10 uM) with other combinations and, even at the highest drug concentrations, CR failed to fully block thioflavin T fluorescence. Importantly, FKBP was required for enhanced potency of SLF-CR; in the absence of FKBP, SLF-CR and CR had similar activity. The efficacy of CR was not, however, influenced by the addition of FKBP. Increasing the molar equivalents of FKBP further enhanced the potency of SLF-CR. These results support that drug-mediated recruitment of FKBP to Aβ is required for enhanced potency.

To independently assess fibril formation, we explored the ultrastructure of Aβ aggregates after drug treatments by direct imaging methods, both transmission electron microscopy (TEM) and atomic force microscopy (AFM). Using TEM, we confirmed that FKBP does not influence the formation or architecture of Aβ fibrils. At a concentration of 1 uM, CR, SLF-CR, and CR/FKBP were ineffective at reducing the size or abundance of Aβ fibrils. However, consistent with the thioflavin T and turbidity experiments, SLF-CR/FKBP almost fully blocked fibril formation. Occasional fibrils remained in these samples and these tended to be structurally similar to those seen in untreated samples. These rare fibrils suggest that some Aβ escapes inhibition and that this peptide aggregates normally.

Recent evidence has strongly suggested a role for non-fibrillar Aβ aggregates in the pathology of Alzheimer's disease. Blocking fibril formation at a stage that leads to accumulation of these highly neurotoxic intermediates would likely have deleterious effects. Preventing formation of these intermediates is therefore an important measure of inhibitory potency. To gain a more detailed understanding of the function of SLF-CR/FKBP, we examined drug-treated mixtures by AFM, which provides three-dimensional information about Aβ aggregates. Consistent with the results from TEM, the samples containing only Aβ(1-42) and FKBP contained a meshwork of elongated fibrils. In contrast, the samples that were additionally treated with SLF-CR failed to form fibrils. Rather, smaller and less elongated species were observed. It appears that these likely represent an intermediate that is trapped prior to formation of Aβ fibrils. The particles are approximately uniform in size (28±5 nm$^2$; N=50), which suggests that SLFCR/FKBP interrupts fibril formation by acting at a discrete step in the aggregation pathway. Because these species are not observed in samples treated with CR/FKBP, it appears that they represent a qualitative difference between the mechanism of action of CR and SLF-CR/FKBP.

While a strategy that interrupts the aggregation process provides mechanistic insight, the most important criterion of therapeutic potential is the capacity to prevent the formation of neurotoxic Aβ aggregates. Hence, we examined whether the bifunctional drugs could inhibit neurotoxicity of in vitro-aggregated Aβ on primary neurons. Cell viability of P0 rat hippocampal neurons was assessed with the 3-(4,5-dimethyl-2-thiazoyl)-2,5 diphenyltetrazoliumbromide (MTT) reduction assay. SLF-CR/FKBP-treated Aβ samples were substantially less toxic than untreated- or CR/FKBP-treated samples. Specifically, SLF-CR/FKBP displayed an $EC_{50}$ approximately 4-fold better than CR/FKBP (0.9±1.3 uM and 4.2±1.4 uM, respectively). SLF-CR's ability to prevent Aβ induced neuronal death was dependent on the concentration of FKBP. These findings support the conclusion that drug mediated recruitment of FKBP not only blocks aggregation but also inhibits Aβ toxicity.

To examine the morphology of the treated neurons, we applied Aβ and drug/protein combinations to cultured hippocampal neurons. Cell death was measured after two days by counting the Tunel positive nuclei. We assessed cell morphology by staining with anti-β-III tubulin antibody. As expected, the potent toxin, camptothecin, induced cell death (36% of the remaining cells were positive for Tunel) as well as abnormal cell morphology. Treatment with Aβ yielded a similar result; neurites became severly dystrophic, some neurons detached from the slides, and those remaining demonstrated signs of nuclear fragmentation and membrane blebbing. Incubation of Aβ with FKBP, CR, CR/FKBP, or SLF-CR prior to addition to the cells failed to substantially reduce the number of Tunel positive cells or prevent changes in cell morphology. The SLF-CR/FKBP combination, however, markedly blocked toxicity. Moreover, cells that were protected by SLFCR/FKBP treatment display mostly normal nuclear and axonal morphology. These studies support the MTT results and demonstrate that FKBP recruitment can protect cultured neurons from cell death triggered by toxic aggregates of Aβ.

Figure 10:
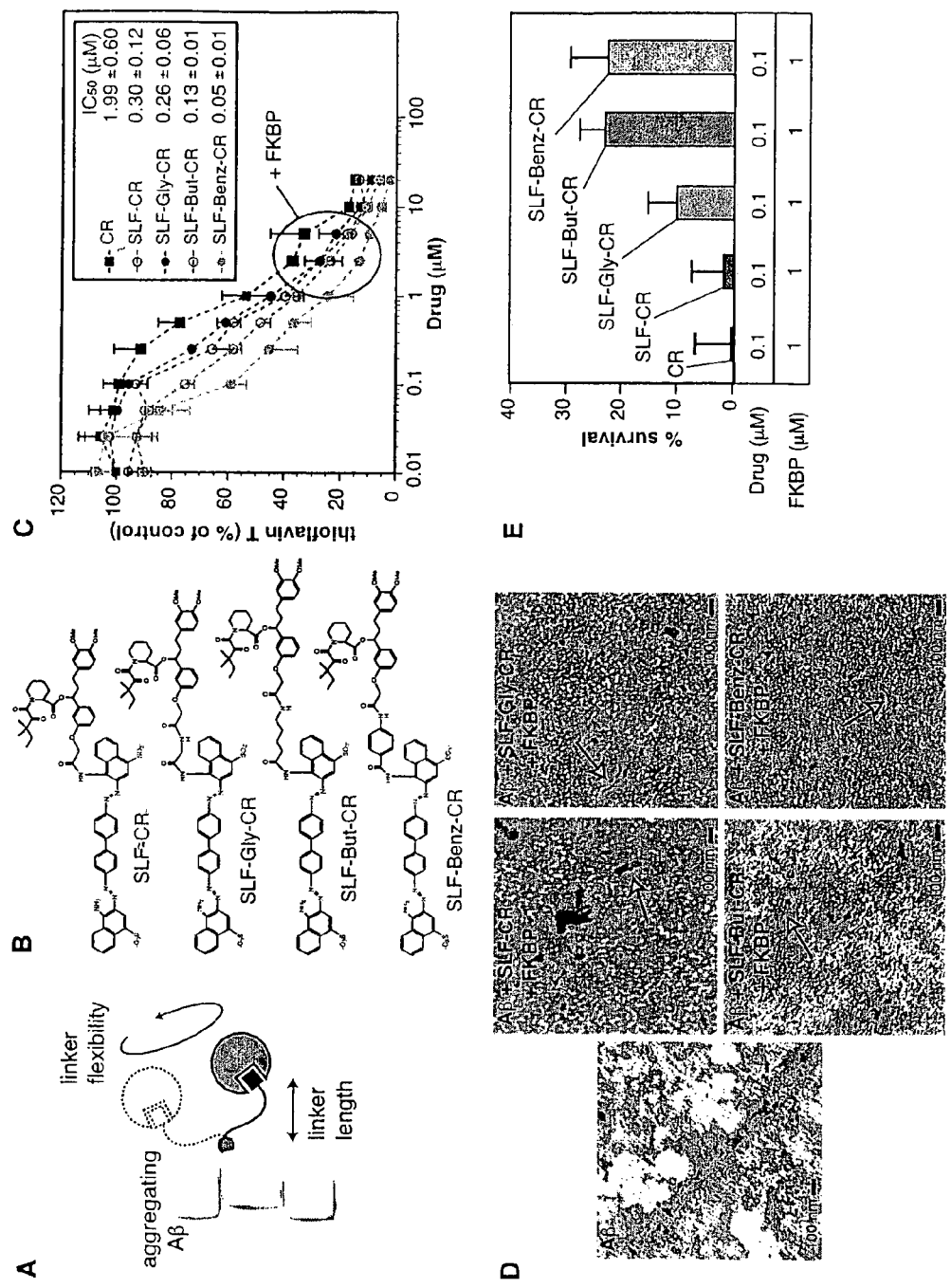
FIG. 10 illustrates: (A) Schematic representation of how improvements in linker length or flexibility can allow bound FKBP to sample a greater area around the Aβ surface. (B) Chemical structures of bifunctional inhibitors generated for the study, with the variable linker region shown in blue and SLF-CR shown for comparison. (C) Relative potency of the bifunctional linker series, as measured by thioflavin T fluorescence. FKBP was added to each aggregation reaction at a final concentration of 1 µM. The average $IC_{50}$ (±SEM) of two experiments performed in triplicate is shown in the inset. (D) TEM images confirm the presence of intermediate particles in Aβ samples treated with SLF-CR/FKBP. Particles of similar size and shape are observed in samples treated with compounds from the linker series. Drug and FKBP concentrations are 0.5 µM and 1 µM, respectively. An untreated Aβ sample is shown. (E) The survival of hippocampal neurons subjected to Aβ samples that had been treated with compounds from the bifunctional linker series. Results are the average (±SEM) of 1 to 2 experiments performed in triplicate.

The subject strategy is designed to allow Aβ-bound bifunctional drugs to wield the steric bulk of FKBP and, thus, prevent nearby Aβ from joining the nascent fibril. A prediction of this hypothesis is that improved coverage of the Aβ surface might provide superior inhibition. This might be achieved by altering the orientation or steric arrangement of FKBP relative to the Aβ surface. Our synthetic strategy permits the assembly of bifunctional compounds from a collection of modular targeting domains, recruiting domains, and interchangeable linkers. Therefore, we envisioned that, by installing linkers that vary in length and flexibility, we might identify compounds that permit FKBP to scan the Aβ surface for favorable arrangements (FIG. 10A).

The methods used to generate the compounds were similar to those used to create SLF-CR by EDC/NHS methods and purified by silica gel chromatography. The resulting SLFs with installed linkers were coupled to CR, purified and characterized as above. In a search for more potent inhibitors, we generated a series of bifunctional compounds that vary in the linker employed (FIG. 10B). These molecules are named according to the reagent used to create the linker (i.e. the amino acid glycine was used to generate SLF-Gly-CR). When we tested these compounds in conjunction with FKBP in the thioflavin T assay, we found that SLF-But-CR/FKBP and SLF-Benz-CR/FKBP are potent inhibitors (FIG. 10C). The most active compound, SLFBenz-CR/FKBP, has an $IC_{50}$ of approximately 50 nM. This value is 40-fold better than CR/FKBP and a 6-fold improvement over the parent combination, SLF-CR/FKBP. Like SLF-CR, the potency of the compounds was dependent on the availability of FKBP. Interestingly, TEM revealed that the size and shape of the intermediates formed in Aβ samples treated with the bifunctional molecules were similar (FIG. 10D). This result suggests that, regardless of the properties of the linker, a common FKBP/drug/Aβ complex is formed.

To explore the role of the linker in reduction of Aβ toxicity, we measured primary neuron viability in response to pre-treated Aβ samples. Consistent with the rank-order as measured by thioflavin T fluorescence, SLF-Benz-CR/FKBP and SLF-But-CR/FKBP were, at nanomolar concentrations, significantly more potent than CR/FKBP or SLF-CR/FKBP (FIG. 10E). Even at the high molar concentrations of Aβ used in these experiments, in which most neurons are killed and CR is unable to rescue them, SLF-Benz-CR remained active at 100 nM. Despite the modest number of compounds in the linker series, these results indicate that potent inhibitors of toxicity can be uncovered by the combinatorial assembly of modular components.

Our results indicate that recruitment of chaperones can block Aβ fibril formation and substantially reduce Aβ toxicity. While other inhibitors of Aβ aggregation, such as CR and short peptides, are active in the 2000 to 10000 nM range, our best compound is potent at 50 nM. The advantage of therapeutic intervention at the aggregation step is that it targets a purely pathological event in disease development. Thus, directly inhibiting Aβ aggregation with the recruited chaperone approach can provide a viable complement to recent efforts to reduce the rate of Aβ release (Citron, Neurobiol Aging 2002 23, 1017-22; Michaelis, J Pharmacol Exp Therapeutics 2003, 304, 897-904), enhance its clearance (Janus, et al., Biochim Biophys Acta 2000, 1502, 63-75; Kayed, et al., Science 2003, 300, 486-9) and/or template non-toxic aggregates (Ghanta, et al., J Biol Chem 1996, 271, 29525-8; Sacchettini and Kelly, Nature Rev Drug Discovery 2002, 1. 267-75; Cohen and Kelly, Nature 2003, 426, 905-9).

It is evident from the above results that the subject compounds and methods provide for a robust ability to investigate the manner of aggregation and toxicity of neurodegenerative proteins. One can also use the subject compounds as standards in competitive assays, using the conjugate in the presence and absence of the disaggregating element, to evaluate test compounds as to their competitiveness in binding and disassociating aggregates, the effect on the formation of aggregation and their effect on neurotoxicity. The subject agents can be prepared from known compounds whose physiology are known and can serve in test animals as to their effect, as well as providing a basis for therapies for the various neurodegenerative diseases.

In addition, the subject strategy provides for compounds that can be used in various situations or contexts where aggregation formation is detrimental to the situation. With complex mixtures, such as lysates, aggregation formation can interfere with assaying the mixture for one or more components, obscure the signal from the mixture or the like. By using the subject strategy, small molecules can be added to the mixture and either endogenous or exogenous proteins recruited to impede or diminish the presence of aggregates. The subject strategy also provides for the recruitment of enzymes to an aggregate, where one is interested in modifying the aggregation as a result of enzymatic activity. As demonstrated with the Aβ aggregates, recruitment of prolyl isomerase can act to modify the prolyl groups of the members of the aggregate with apparent modification of the presence of aggregates.

All references referred to in the text are incorporated herein by reference as if fully set forth herein. The relevant portions associated with this document will be evident to those of skill in the art. Any discrepancies between this application and such reference will be resolved in favor of the view set forth in this application.

Although the invention has been described with reference to the above examples, it will be understood that modifications and variations are encompassed within the spirit and scope of the invention. Accordingly, the invention is limited only by the following claims.

What is claimed is:

1. A compound of the formula:

R1-L-R2, wherein R1 is a monovalent moiety of a compound selected from the group consisting of thioflavin, thioflavin T, chrysamine G, and Congo red;

L is a bond or linking group of not more than about 36 atoms other than hydrogen; and R2 is a monovalent moiety of a compound selected from the group consisting of SLF, FK506 and rapamycin.

2. A compound according to claim 1, wherein L is a p-aminobenzamide.

3. A compound according to claim 1, wherein R1 is a monovalent moiety of Congo Red.

4. A compound according to claim 1, wherein R1 is a monovalent moiety of chrysamine G.

5. A compound according to claim 1, wherein R2 is a monovalent moiety of SLF.

* * * * *